United States Patent [19]
Fukui et al.

[11] Patent Number: 5,981,257
[45] Date of Patent: Nov. 9, 1999

[54] POLYESTER SYNTHASE GENE AND PROCESS FOR PRODUCING POLYESTER

[75] Inventors: Toshiaki Fukui; Yoshiharu Doi, both of Saitama, Japan

[73] Assignee: The Institute of Physical & Chemical Research, Saitama, Japan

[21] Appl. No.: 08/910,856

[22] Filed: Aug. 13, 1997

[30] Foreign Application Priority Data

Aug. 14, 1996 [JP] Japan .................................... 8-214509
Jul. 25, 1997 [JP] Japan .................................... 9-199979

[51] Int. Cl.$^6$ ............................... C12N 9/88; C12N 1/20; C12N 15/00; C07H 21/04

[52] U.S. Cl. ...................... 435/232; 536/23.2; 536/23.7; 435/69.1; 435/252.3; 435/320.1; 530/350

[58] Field of Search ................................. 435/232, 252.3, 435/320.1, 69.1; 536/23.2, 23.7; 530/350

[56] References Cited

PUBLICATIONS

Schbert et al. J. Bacteriol. 173 (1): 168–175, Jan. 1998.

*Primary Examiner*—Ponnathapura Achutamurthy
*Assistant Examiner*—Tekchand Saidha
*Attorney, Agent, or Firm*—Fish & Richardson P.C.

[57] ABSTRACT

The present invention relates to a polyester synthase gene coding for a polypeptide containing the amino acid sequence of SEQ ID NO:2 or a sequence where in the amino acid sequence of SEQ ID NO:2, one or more amino acids are deleted, replaced or added, the polypeptide bringing about polyester synthase activity; a gene expression cassette comprising the polyester synthase gene and either of open reading frames located upstream and downstream of the gene; a recombinant vector comprising the gene expression cassette; a transformant transformed with the recombinant vector; and a process for producing polyester by culturing the transformant in a medium and recovering polyester from the resulting culture.

13 Claims, 2 Drawing Sheets

Lane M: molecular-weight marker

Lane 1: soluble-protein fraction from NB3

Lane 2: active fraction eluted from the anion exchange column

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
       (A) LENGTH: 1785 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION:1..1782

(xi) SEQUENCE DESCRIPTION: SEQ ID NO: 1:

```
ATG AGC CAA CCA TCT TAT GGC CCG CTG TTC GAG GCC CTG GCC CAC TAC         48
Met Ser Gln Pro Ser Tyr Gly Pro Leu Phe Glu Ala Leu Ala His Tyr
 1               5                  10                  15

AAT GAC AAG CTG CTG GCC ATG GCC AAG GCC CAG ACA GAG CGC ACC GCC         96
Asn Asp Lys Leu Leu Ala Met Ala Lys Ala Gln Thr Glu Arg Thr Ala
                 20                  25                  30

CAG GCG CTG CTG CAG ACC AAT CTG GAC GAT CTG GGC CAG GTG CTG GAG        144
```

```
           Gln Ala Leu Leu Gln Thr Asn Leu Asp Asp Leu Gly Gln Val Leu Glu
                        35                  40                  45

CAG GGC AGC CAG CAA CCC TGG CAG CTG ATC CAG GCC CAG ATG AAC TGG                 192
Gln Gly Ser Gln Gln Pro Trp Gln Leu Ile Gln Ala Gln Met Asn Trp
         50                  55                  60

TGG CAG GAT CAG CTC AAG CTG ATG CAG CAC ACC CTG CTC AAA AGC GCA                 240
Trp Gln Asp Gln Leu Lys Leu Met Gln His Thr Leu Leu Lys Ser Ala
65                  70                  75                  80

GGC CAG CCG AGC GAG CCG GTG ATC ACC CCG GAG CGC AGC GAT CGC CGC                 288
Gly Gln Pro Ser Glu Pro Val Ile Thr Pro Glu Arg Ser Asp Arg Arg
                    85                  90                  95

TTC AAG GCC GAG GCC TGG AGC GAA CAA CCC ATC TAT GAC TAC CTC AAG                 336
Phe Lys Ala Glu Ala Trp Ser Glu Gln Pro Ile Tyr Asp Tyr Leu Lys
                100                 105                 110

CAG TCC TAC CTG CTC ACC GCC AGG CAC CTG CTG GCC TCG GTG GAT GCC                 384
Gln Ser Tyr Leu Leu Thr Ala Arg His Leu Leu Ala Ser Val Asp Ala
            115                 120                 125

CTG GAG GGC GTC CCC CAG AAG AGC CGG GAG CGG CTG CGT TTC TTC ACC                 432
Leu Glu Gly Val Pro Gln Lys Ser Arg Glu Arg Leu Arg Phe Phe Thr
130                 135                 140

CGC CAG TAC GTC AAC GCC ATG GCC CCC AGC AAC TTC CTG GCC ACC AAC                 480
Arg Gln Tyr Val Asn Ala Met Ala Pro Ser Asn Phe Leu Ala Thr Asn
145                 150                 155                 160

CCC GAG CTG CTC AAG CTG ACC CTG GAG TCC GAC GGC CAG AAC CTG GTG                 528
Pro Glu Leu Leu Lys Leu Thr Leu Glu Ser Asp Gly Gln Asn Leu Val
                165                 170                 175

CGC GGA CTG GCC CTC TTG GCC GAG GAT CTG GAG CGC AGC GCC GAT CAG                 576
Arg Gly Leu Ala Leu Leu Ala Glu Asp Leu Glu Arg Ser Ala Asp Gln
                180                 185                 190

CTC AAC ATC CGC CTG ACC GAC GAA TCC GCC TTC GAG CTC GGG CGG GAT                 624
Leu Asn Ile Arg Leu Thr Asp Glu Ser Ala Phe Glu Leu Gly Arg Asp
            195                 200                 205

CTG GCC CTG ACC CCG GGC CGG GTG GTG CAG CGC ACC GAG CTC TAT GAG                 672
Leu Ala Leu Thr Pro Gly Arg Val Val Gln Arg Thr Glu Leu Tyr Glu
210                 215                 220

CTC ATT CAG TAC AGC CCG ACT ACC GAG ACG GTG GGC AAG ACA CCT GTG                 720
Leu Ile Gln Tyr Ser Pro Thr Thr Glu Thr Val Gly Lys Thr Pro Val
225                 230                 235                 240

CTG ATA GTG CCC CCC TTC ATC AAC AAG TAC TAC ATC ATG GAC ATG CGG                 768
Leu Ile Val Pro Pro Phe Ile Asn Lys Tyr Tyr Ile Met Asp Met Arg
                245                 250                 255

CCC CAG AAC TCC CTG GTC GCC TGG CTG GTC GCC CAG GGC CAG ACG GTA                 816
Pro Gln Asn Ser Leu Val Ala Trp Leu Val Ala Gln Gly Gln Thr Val
                260                 265                 270

TTC ATG ATC TCC TGG CGC AAC CCG GGC GTG GCC CAG GCC CAA ATC GAT                 864
Phe Met Ile Ser Trp Arg Asn Pro Gly Val Ala Gln Ala Gln Ile Asp
            275                 280                 285

CTC GAC GAC TAC GTG GTG GAT GGC GTC ATC GCC GCC CTG GAC GGC GTG                 912
Leu Asp Asp Tyr Val Val Asp Gly Val Ile Ala Ala Leu Asp Gly Val
            290                 295                 300

GAG GCG GCC ACC GGC GAG CGG GAG GTG CAC GGC ATC GGC TAC TGC ATC                 960
Glu Ala Ala Thr Gly Glu Arg Glu Val His Gly Ile Gly Tyr Cys Ile
305                 310                 315                 320

GGC GGC ACC GCC CTG TCG CTC GCC ATG GGC TGG CTG GCG GCG CGG CGC                1008
Gly Gly Thr Ala Leu Ser Leu Ala Met Gly Trp Leu Ala Ala Arg Arg
                325                 330                 335

CAG AAG CAG CGG GTG CGC ACC GCC ACC CTG TTC ACT ACC CTG CTG GAC                1056
Gln Lys Gln Arg Val Arg Thr Ala Thr Leu Phe Thr Thr Leu Leu Asp
                340                 345                 350

TTC TCC CAG CCC GGG GAG CTT GGC ATC TTC ATC CAC GAG CCC ATC ATA                1104
```

```
Phe Ser Gln Pro Gly Glu Leu Gly Ile Phe Ile His Glu Pro Ile Ile
    355                 360                 365

GCG GCG CTC GAG GCG CAA AAT GAG GCC AAG GGC ATC ATG GAC GGG CGC    1152
Ala Ala Leu Glu Ala Gln Asn Glu Ala Lys Gly Ile Met Asp Gly Arg
370                 375                 380

CAG CTG GCG GTC TCC TTC AGC CTG CTG CGG GAG AAC AGC CTC TAC TGG    1200
Gln Leu Ala Val Ser Phe Ser Leu Leu Arg Glu Asn Ser Leu Tyr Trp
385                 390                 395                 400

AAC TAC TAC ATC GAC AGC TAC CTC AAG GGT CAG AGC CCG GTG GCC TTC    1248
Asn Tyr Tyr Ile Asp Ser Tyr Leu Lys Gly Gln Ser Pro Val Ala Phe
                405                 410                 415

GAT CTG CTG CAC TGG AAC AGC GAC AGC ACC AAT GTG GCG GGC AAG ACC    1296
Asp Leu Leu His Trp Asn Ser Asp Ser Thr Asn Val Ala Gly Lys Thr
                420                 425                 430

CAC AAC AGC CTG CTG CGC CGT CTC TAC CTG GAG AAC CAG CTG GTG AAG    1344
His Asn Ser Leu Leu Arg Arg Leu Tyr Leu Glu Asn Gln Leu Val Lys
            435                 440                 445

GGG GAG CTC AAG ATC CGC AAC ACC CGC ATC GAT CTC GGC AAG GTG AAG    1392
Gly Glu Leu Lys Ile Arg Asn Thr Arg Ile Asp Leu Gly Lys Val Lys
450                 455                 460

ACC CCT GTG CTG CTG GTG TCG GCG GTG GAC GAT CAC ATC GCC CTC TGG    1440
Thr Pro Val Leu Leu Val Ser Ala Val Asp Asp His Ile Ala Leu Trp
465                 470                 475                 480

CAG GGC ACC TGG CAG GGC ATG AAG CTG TTT GGC GGG GAG CAG CGC TTC    1488
Gln Gly Thr Trp Gln Gly Met Lys Leu Phe Gly Gly Glu Gln Arg Phe
                485                 490                 495

CTC CTG GCG GAG TCC GGC CAC ATC GCC GGC ATC ATC AAC CCG CCG GCC    1536
Leu Leu Ala Glu Ser Gly His Ile Ala Gly Ile Ile Asn Pro Pro Ala
                500                 505                 510

GCC AAC AAG TAC GGC TTC TGG CAC AAC GGG GCC GAG GCC GAG AGC CCG    1584
Ala Asn Lys Tyr Gly Phe Trp His Asn Gly Ala Glu Ala Glu Ser Pro
            515                 520                 525

GAG AGC TGG CTG GCA GGG GCG ACG CAC CAG GGC GGC TCC TGG TGG CCC    1632
Glu Ser Trp Leu Ala Gly Ala Thr His Gln Gly Gly Ser Trp Trp Pro
530                 535                 540

GAG ATG ATG GGC TTT ATC CAG AAC CGT GAC GAA GGG TCA GAG CCC GTC    1680
Glu Met Met Gly Phe Ile Gln Asn Arg Asp Glu Gly Ser Glu Pro Val
545                 550                 555                 560

CCC GCG CGG GTC CCG GAG GAA GGG CTG GCC CCC GCC CCC GGC CAC TAT    1728
Pro Ala Arg Val Pro Glu Glu Gly Leu Ala Pro Ala Pro Gly His Tyr
                565                 570                 575

GTC AAG GTG CGG CTC AAC CCC GTG TTT GCC TGC CCA ACA GAG GAG GAC    1776
Val Lys Val Arg Leu Asn Pro Val Phe Ala Cys Pro Thr Glu Glu Asp
                580                 585                 590

GCC GCA TGA                                                         1785
Ala Ala
```

(2) INFORMATION FOR SEQ ID NO: 2:

(i) SEQUENCE CHARACTERISTICS:
        (A) LENGTH: 594 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 2:

```
Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30
```

```
Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
 50                  55                  60

Trp Gln Asp Gln Leu Lys Leu Met Gln His Thr Leu Leu Lys Ser Ala
 65                  70                  75                  80

Gly Gln Pro Ser Glu Pro Val Ile Thr Pro Glu Arg Ser Asp Arg Arg
                 85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
```

```
            450                 455                 460
Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
                500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
        530                 535                 540

Glu Met Met Gly Phe Ile Gln Asn Arg Asp Glu Gly Ser Glu Pro Val
545                 550                 555                 560

Pro Ala Arg Val Pro Glu Gly Leu Ala Pro Ala Pro Gly His Tyr
                565                 570                 575

Val Lys Val Arg Leu Asn Pro Val Phe Ala Cys Pro Thr Glu Glu Asp
                580                 585                 590

Ala Ala
```

(2) INFORMATION FOR SEQ ID NO: 3:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..351

(xi) SEQUENCE DESCRIPTION: SEQ ID NO: 3:

```
ATG ATG AAT ATG GAC GTG ATC AAG AGC TTT ACC GAG CAG ATG CAA GGC        48
Met Met Asn Met Asp Val Ile Lys Ser Phe Thr Glu Gln Met Gln Gly
1               5                   10                  15

TTC GCC GCC CCC CTC ACC CGC TAC AAC CAG CTG CTG GCC AGC AAC ATC        96
Phe Ala Ala Pro Leu Thr Arg Tyr Asn Gln Leu Leu Ala Ser Asn Ile
                20                  25                  30

GAA CAG CTG ACC CGG TTG CAG CTG GCC TCC GCC AAC GCC TAC GCC GAA       144
Glu Gln Leu Thr Arg Leu Gln Leu Ala Ser Ala Asn Ala Tyr Ala Glu
            35                  40                  45

CTG GGC CTC AAC CAG TTG CAG GCC GTG AGC AAG GTG CAG GAC ACC CAG       192
Leu Gly Leu Asn Gln Leu Gln Ala Val Ser Lys Val Gln Asp Thr Gln
        50                  55                  60

AGC CTG GCG GCC CTG GGC ACA GTG CAA CTG GAG ACC GCC AGC CAG CTC       240
Ser Leu Ala Ala Leu Gly Thr Val Gln Leu Glu Thr Ala Ser Gln Leu
65                  70                  75                  80

TCC CGC CAG ATG CTG GAT GAC ATC CAG AAG CTG AGC GCC CTC GGC CAG       288
Ser Arg Gln Met Leu Asp Asp Ile Gln Lys Leu Ser Ala Leu Gly Gln
                85                  90                  95

CAG TTC AAG GAA GAG CTG GAT GTC CTG ACC GCA GAC GGC ATC AAG AAA       336
Gln Phe Lys Glu Glu Leu Asp Val Leu Thr Ala Asp Gly Ile Lys Lys
                100                 105                 110

AGC ACG GGC AAG GCC TGA                                               354
Ser Thr Gly Lys Ala
            115
```

(2) INFORMATION FOR SEQ ID NO: 4:

(i) SEQUENCE CHARACTERISTICS:
    (A) LENGTH: 117 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO: 4:

```
Met Met Asn Met Asp Val Ile Lys Ser Phe Thr Glu Gln Met Gln Gly
 1               5                  10                  15

Phe Ala Ala Pro Leu Thr Arg Tyr Asn Gln Leu Leu Ala Ser Asn Ile
                20                  25                  30

Glu Gln Leu Thr Arg Leu Gln Leu Ala Ser Ala Asn Ala Tyr Ala Glu
            35                  40                  45

Leu Gly Leu Asn Gln Leu Gln Ala Val Ser Lys Val Gln Asp Thr Gln
    50                  55                  60

Ser Leu Ala Ala Leu Gly Thr Val Gln Leu Glu Thr Ala Ser Gln Leu
 65                  70                  75                  80

Ser Arg Gln Met Leu Asp Asp Ile Gln Lys Leu Ser Ala Leu Gly Gln
                85                  90                  95

Gln Phe Lys Glu Glu Leu Asp Val Leu Thr Ala Asp Gly Ile Lys Lys
            100                 105                 110

Ser Thr Gly Lys Ala
        115
```

(2) INFORMATION FOR SEQ ID NO: 5:

(i) SEQUENCE CHARACTERISTICS:
       (A) LENGTH: 405 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION:1..402

(xi) SEQUENCE DESCRIPTION: SEQ ID NO: 5:

```
ATG AGC GCA CAA TCC CTG GAA GTA GGC CAG AAG GCC CGT CTC AGC AAG      48
Met Ser Ala Gln Ser Leu Glu Val Gly Gln Lys Ala Arg Leu Ser Lys
 1               5                  10                  15

CGG TTC GGG GCG GCG GAG GTA GCC GCC TTC GCC GCG CTC TCG GAG GAC      96
Arg Phe Gly Ala Ala Glu Val Ala Ala Phe Ala Ala Leu Ser Glu Asp
                20                  25                  30

TTC AAC CCC CTG CAC CTG GAC CCG GCC TTC GCC GCC ACC ACG GCG TTC     144
Phe Asn Pro Leu His Leu Asp Pro Ala Phe Ala Ala Thr Thr Ala Phe
            35                  40                  45

GAG CGG CCC ATA GTC CAC GGC ATG CTG CTC GCC AGC CTC TTC TCC GGG     192
Glu Arg Pro Ile Val His Gly Met Leu Leu Ala Ser Leu Phe Ser Gly
    50                  55                  60

CTG CTG GGC CAG CAG TTG CCG GGC AAG GGG AGC ATC TAT CTG GGT CAA     240
Leu Leu Gly Gln Gln Leu Pro Gly Lys Gly Ser Ile Tyr Leu Gly Gln
 65                  70                  75                  80

AGC CTC AGC TTC AAG CTG CCG GTC TTT GTC GGG GAC GAG GTG ACG GCC     288
Ser Leu Ser Phe Lys Leu Pro Val Phe Val Gly Asp Glu Val Thr Ala
                85                  90                  95

GAG GTG GAG GTG ACC GCC CTT CGC GAG GAC AAG CCC ATC GCC ACC CTG     336
Glu Val Glu Val Thr Ala Leu Arg Glu Asp Lys Pro Ile Ala Thr Leu
            100                 105                 110

ACC ACC CGC ATC TTC ACC CAA GGC GGC GCC CTC GCC GTG ACG GGG GAA     384
```

```
Thr Thr Arg Ile Phe Thr Gln Gly Gly Ala Leu Ala Val Thr Gly Glu
    115                 120                 125

GCC GTG GTC AAG CTG CCT TAA                                                      405
Ala Val Val Lys Leu Pro
    130
```

(2) INFORMATION FOR SEQ ID NO: 6:

(i) SEQUENCE CHARACTERISTICS:
        (A) LENGTH: 134 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 6:

```
Met Ser Ala Gln Ser Leu Glu Val Gly Gln Lys Ala Arg Leu Ser Lys
 1               5                  10                  15

Arg Phe Gly Ala Ala Glu Val Ala Ala Phe Ala Ala Leu Ser Glu Asp
            20                  25                  30

Phe Asn Pro Leu His Leu Asp Pro Ala Phe Ala Ala Thr Thr Ala Phe
                35                  40                  45

Glu Arg Pro Ile Val His Gly Met Leu Leu Ala Ser Leu Phe Ser Gly
    50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
            100                 105                 110

Thr Thr Arg Ile Phe Thr Gln Gly Gly Ala Leu Ala Val Thr Gly Glu
    115                 120                 125

Ala Val Val Lys Leu Pro
    130
```

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 7:

```
CCSCCSTGGA TCAAYAAGTW YTAYATC                                                    27
```

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 8:

```
SAGCCASGCS GTCCARTCSG GCCACCA                                                    27
```

(2) INFORMATION FOR SEQ ID NO: 9:

(i) SEQUENCE CHARACTERISTICS:
        (A) LENGTH: 3187 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 384..734

(ix) FEATURE:
        (A) NAME/KEY: CDS
        (B) LOCATION: 830..2611

(xi) SEQUENCE DESCRIPTION: SEQ ID NO: 9:

```
AGATCTGGAC CGGGGTGCTG GCCTGGGCCA CGCCGGCGAG GGCCAGCGCG GAGCAACCGA      60

GCAGCAGGGC GAGAGGTTTC ATCGGGATTC CTTGGCAGTC TGAATGACGT GCCAGCCTAT     120

CAGCGCGGCG CCGGTGCGGC GAGGGCGCGC CGGACCCAGT GCGTCACCTC TCGTCTGATC     180

CGCCTCCCTC GACGGGCGTC GCTGACAAAA AAATTCAAAC AGAAATTAAC ATTTATGTCA     240

TTTACACCAA ACCGCATTTG GTTGCAGAAT GCTCAAACGT GTGTTTGAAC AGAGCAAGCA     300

ACACGTAAAC AGGGATGACA TGCAGTACCC GTAAGAAGGG CCGATTGGCC CACAACAACA     360

CTGTTCTGCC GAACTGGAGA CCG ATG ATG AAT ATG GAC GTG ATC AAG AGC         410
                        Met Met Asn Met Asp Val Ile Lys Ser
                         1               5

TTT ACC GAG CAG ATG CAA GGC TTC GCC GCC CCC CTC ACC CGC TAC AAC       458
Phe Thr Glu Gln Met Gln Gly Phe Ala Ala Pro Leu Thr Arg Tyr Asn
 10              15                  20                  25

CAG CTG CTG GCC AGC AAC ATC GAA CAG CTG ACC CGG TTG CAG CTG GCC       506
Gln Leu Leu Ala Ser Asn Ile Glu Gln Leu Thr Arg Leu Gln Leu Ala
                 30                  35                  40

TCC GCC AAC GCC TAC GCC GAA CTG GGC CTC AAC CAG TTG CAG GCC GTG       554
Ser Ala Asn Ala Tyr Ala Glu Leu Gly Leu Asn Gln Leu Gln Ala Val
             45                  50                  55

AGC AAG GTG CAG GAC ACC CAG AGC CTG GCG GCC CTG GGC ACA GTG CAA       602
Ser Lys Val Gln Asp Thr Gln Ser Leu Ala Ala Leu Gly Thr Val Gln
         60                  65                  70

CTG GAG ACC GCC AGC CAG CTC TCC CGC CAG ATG CTG GAT GAC ATC CAG       650
Leu Glu Thr Ala Ser Gln Leu Ser Arg Gln Met Leu Asp Asp Ile Gln
     75                  80                  85

AAG CTG AGC GCC CTC GGC CAG CAG TTC AAG GAA GAG CTG GAT GTC CTG       698
Lys Leu Ser Ala Leu Gly Gln Gln Phe Lys Glu Glu Leu Asp Val Leu
 90                  95                 100                 105

ACC GCA GAC GGC ATC AAG AAA AGC ACG GGC AAG GCC TGATAACCCC            744
Thr Ala Asp Gly Ile Lys Lys Ser Thr Gly Lys Ala
                 110                 115

TGGCTGCCCG TTCGGGCAGC CACATCTCCC CATGACTCGA CGCTACGGGC TAGTTCCCGC     804

CTCGGGTGTG GGTGAAGGAG AGCAC ATG AGC CAA CCA TCT TAT GGC CCG CTG       856
                            Met Ser Gln Pro Ser Tyr Gly Pro Leu
                             1               5

TTC GAG GCC CTG GCC CAC TAC AAT GAC AAG CTG CTG GCC ATG GCC AAG       904
Phe Glu Ala Leu Ala His Tyr Asn Asp Lys Leu Leu Ala Met Ala Lys
 10                  15                  20                  25

GCC CAG ACA GAG CGC ACC GCC CAG GCG CTG CTG CAG ACC AAT CTG GAC       952
Ala Gln Thr Glu Arg Thr Ala Gln Ala Leu Leu Gln Thr Asn Leu Asp
                 30                  35                  40

GAT CTG GGC CAG GTG CTG GAG CAG GGC AGC CAG CAA CCC TGG CAG CTG      1000
Asp Leu Gly Gln Val Leu Glu Gln Gly Ser Gln Gln Pro Trp Gln Leu
```

```
                         45                  50                  55
ATC CAG GCC CAG ATG AAC TGG TGG CAG GAT CAG CTC AAG CTG ATG CAG      1048
Ile Gln Ala Gln Met Asn Trp Trp Gln Asp Gln Leu Lys Leu Met Gln
                 60                  65                  70

CAC ACC CTG CTC AAA AGC GCA GGC CAG CCG AGC GAG CCG GTG ATC ACC      1096
His Thr Leu Leu Lys Ser Ala Gly Gln Pro Ser Glu Pro Val Ile Thr
         75                  80                  85

CCG GAG CGC AGC GAT CGC CGC TTC AAG GCC GAG GCC TGG AGC GAA CAA      1144
Pro Glu Arg Ser Asp Arg Arg Phe Lys Ala Glu Ala Trp Ser Glu Gln
 90                  95                 100                 105

CCC ATC TAT GAC TAC CTC AAG CAG TCC TAC CTG CTC ACC GCC AGG CAC      1192
Pro Ile Tyr Asp Tyr Leu Lys Gln Ser Tyr Leu Leu Thr Ala Arg His
             110                 115                 120

CTG CTG GCC TCG GTG GAT GCC CTG GAG GGC GTC CCC CAG AAG AGC CGG      1240
Leu Leu Ala Ser Val Asp Ala Leu Glu Gly Val Pro Gln Lys Ser Arg
                 125                 130                 135

GAG CGG CTG CGT TTC TTC ACC CGC CAG TAC GTC AAC GCC ATG GCC CCC      1288
Glu Arg Leu Arg Phe Phe Thr Arg Gln Tyr Val Asn Ala Met Ala Pro
         140                 145                 150

AGC AAC TTC CTG GCC ACC AAC CCC GAG CTG CTC AAG CTG ACC CTG GAG      1336
Ser Asn Phe Leu Ala Thr Asn Pro Glu Leu Leu Lys Leu Thr Leu Glu
155                 160                 165

TCC GAC GGC CAG AAC CTG GTG CGC GGA CTG GCC CTC TTG GCC GAG GAT      1384
Ser Asp Gly Gln Asn Leu Val Arg Gly Leu Ala Leu Leu Ala Glu Asp
170                 175                 180                 185

CTG GAG CGC AGC GCC GAT CAG CTC AAC ATC CGC CTG ACC GAC GAA TCC      1432
Leu Glu Arg Ser Ala Asp Gln Leu Asn Ile Arg Leu Thr Asp Glu Ser
                 190                 195                 200

GCC TTC GAG CTC GGG CGG GAT CTG GCC CTG ACC CCG GGC CGG GTG GTG      1480
Ala Phe Glu Leu Gly Arg Asp Leu Ala Leu Thr Pro Gly Arg Val Val
         205                 210                 215

CAG CGC ACC GAG CTC TAT GAG CTC ATT CAG TAC AGC CCG ACT ACC GAG      1528
Gln Arg Thr Glu Leu Tyr Glu Leu Ile Gln Tyr Ser Pro Thr Thr Glu
             220                 225                 230

ACG GTG GGC AAG ACA CCT GTG CTG ATA GTG CCG CCC TTC ATC AAC AAG      1576
Thr Val Gly Lys Thr Pro Val Leu Ile Val Pro Pro Phe Ile Asn Lys
             235                 240                 245

TAC TAC ATC ATG GAC ATG CGG CCC CAG AAC TCC CTG GTC GCC TGG CTG      1624
Tyr Tyr Ile Met Asp Met Arg Pro Gln Asn Ser Leu Val Ala Trp Leu
250                 255                 260                 265

GTC GCC CAG GGC CAG ACG GTA TTC ATG ATC TCC TGG CGC AAC CCG GGC      1672
Val Ala Gln Gly Gln Thr Val Phe Met Ile Ser Trp Arg Asn Pro Gly
                 270                 275                 280

GTG GCC CAG GCC CAA ATC GAT CTC GAC GAC TAC GTG GTG GAT GGC GTC      1720
Val Ala Gln Ala Gln Ile Asp Leu Asp Asp Tyr Val Val Asp Gly Val
         285                 290                 295

ATC GCC GCC CTG GAC GGC GTG GAG GCG GCC ACC GGC GAG CGG GAG GTG      1768
Ile Ala Ala Leu Asp Gly Val Glu Ala Ala Thr Gly Glu Arg Glu Val
             300                 305                 310

CAC GGC ATC GGC TAC TGC ATC GGC GGC ACC GCC CTG TCG CTC GCC ATG      1816
His Gly Ile Gly Tyr Cys Ile Gly Gly Thr Ala Leu Ser Leu Ala Met
             315                 320                 325

GGC TGG CTG GCG GCG CGG CGC CAG AAG CAG CGG GTG CGC ACC GCC ACC      1864
Gly Trp Leu Ala Ala Arg Arg Gln Lys Gln Arg Val Arg Thr Ala Thr
330                 335                 340                 345

CTG TTC ACT ACC CTG CTG GAC TTC TCC CAG CCC GGG GAG CTT GGC ATC      1912
Leu Phe Thr Thr Leu Leu Asp Phe Ser Gln Pro Gly Glu Leu Gly Ile
                 350                 355                 360

TTC ATC CAC GAG CCC ATC ATA GCG GCG CTC GAG GCG CAA AAT GAG GCC      1960
Phe Ile His Glu Pro Ile Ile Ala Ala Leu Glu Ala Gln Asn Glu Ala
```

```
                       365                  370                  375
AAG GGC ATC ATG GAC GGG CGC CAG CTG GCG GTC TCC TTC AGC CTG CTG       2008
Lys Gly Ile Met Asp Gly Arg Gln Leu Ala Val Ser Phe Ser Leu Leu
            380                  385                  390

CGG GAG AAC AGC CTC TAC TGG AAC TAC TAC ATC GAC AGC TAC CTC AAG       2056
Arg Glu Asn Ser Leu Tyr Trp Asn Tyr Tyr Ile Asp Ser Tyr Leu Lys
        395                  400                  405

GGT CAG AGC CCG GTG GCC TTC GAT CTG CTG CAC TGG AAC AGC GAC AGC       2104
Gly Gln Ser Pro Val Ala Phe Asp Leu Leu His Trp Asn Ser Asp Ser
410                  415                  420                  425

ACC AAT GTG GCG GGC AAG ACC CAC AAC AGC CTG CTG CGC CGT CTC TAC       2152
Thr Asn Val Ala Gly Lys Thr His Asn Ser Leu Leu Arg Arg Leu Tyr
                430                  435                  440

CTG GAG AAC CAG CTG GTG AAG GGG GAG CTC AAG ATC CGC AAC ACC CGC       2200
Leu Glu Asn Gln Leu Val Lys Gly Glu Leu Lys Ile Arg Asn Thr Arg
            445                  450                  455

ATC GAT CTC GGC AAG GTG AAG ACC CCT GTG CTG CTG GTG TCG GCG GTG       2248
Ile Asp Leu Gly Lys Val Lys Thr Pro Val Leu Leu Val Ser Ala Val
        460                  465                  470

GAC GAT CAC ATC GCC CTC TGG CAG GGC ACC TGG CAG GGC ATG AAG CTG       2296
Asp Asp His Ile Ala Leu Trp Gln Gly Thr Trp Gln Gly Met Lys Leu
475                  480                  485

TTT GGC GGG GAG CAG CGC TTC CTC CTG GCG GAG TCC GGC CAC ATC GCC       2344
Phe Gly Gly Glu Gln Arg Phe Leu Leu Ala Glu Ser Gly His Ile Ala
490                  495                  500                  505

GGC ATC ATC AAC CCG CCG GCC GCC AAC AAG TAC GGC TTC TGG CAC AAC       2392
Gly Ile Ile Asn Pro Pro Ala Ala Asn Lys Tyr Gly Phe Trp His Asn
                510                  515                  520

GGG GCC GAG GCC GAG AGC CCG GAG AGC TGG CTG GCA GGG GCG ACG CAC       2440
Gly Ala Glu Ala Glu Ser Pro Glu Ser Trp Leu Ala Gly Ala Thr His
            525                  530                  535

CAG GGC GGC TCC TGG TGG CCC GAG ATG ATG GGC TTT ATC CAG AAC CGT       2488
Gln Gly Gly Ser Trp Trp Pro Glu Met Met Gly Phe Ile Gln Asn Arg
        540                  545                  550

GAC GAA GGG TCA GAG CCC GTC CCC GCG CGG GTC CCG GAG GAA GGG CTG       2536
Asp Glu Gly Ser Glu Pro Val Pro Ala Arg Val Pro Glu Glu Gly Leu
555                  560                  565

GCC CCC GCC CCC GGC CAC TAT GTC AAG GTG CGG CTC AAC CCC GTG TTT       2584
Ala Pro Ala Pro Gly His Tyr Val Lys Val Arg Leu Asn Pro Val Phe
570                  575                  580                  585

GCC TGC CCA ACA GAG GAG GAC GCC GCA TGAGCGCACA ATCCCTGGAA             2631
Ala Cys Pro Thr Glu Glu Asp Ala Ala
                590

GTAGGCCAGA AGGCCCGTCT CAGCAAGCGG TTCGGGGCGG CGGAGGTAGC CGCCTTCGCC     2691

GCGCTCTCGG AGGACTTCAA CCCCCTGCAC CTGGACCCGG CCTTCGCCGC CACCACGGCG     2751

TTCGAGCGGC CCATAGTCCA CGGCATGCTG CTCGCCAGCC TCTTCTCCGG GCTGCTGGGC     2811

CAGCAGTTGC CGGGCAAGGG GAGCATCTAT CTGGGTCAAA GCCTCAGCTT CAAGCTGCCG     2871

GTCTTTGTCG GGACGAGGT GACGGCCGAG GTGGAGGTGA CCGCCCTTCG CGAGGACAAG      2931

CCCATCGCCA CCCTGACCAC CCGCATCTTC ACCCAAGGCG CGCCCCTCGC CGTGACGGGG     2991

GAAGCCGTGG TCAAGCTGCC TTAAGCACCG GCGGCACGCA GGCACAATCA GCCCGGCCCC    3051

TGCCGGGCTG ATTGTTCTCC CCCGCTCCGC TTGCCCCCTT TTTCGGGGCA ATTTGGCCCA     3111

GGCCCTTTCC CTGCCCCGCC TAACTGCCTA AAATGGCCGC CCTGCCGTGT AGGCATTCAT     3171

CCAGCTAGAG GAATTC                                                    3187

(2) INFORMATION FOR SEQ ID NO: 10:
```

(i) SEQUENCE CHARACTERISTICS:
    (A) LENGTH: 3187 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 2611..3012

(xi) SEQUENCE DESCRIPTION: SEQ ID NO: 10:

```
AGATCTGGAC CGGGGTGCTG GCCTGGGCCA CGCCGGCGAG GGCCAGCGCG GAGCAACCGA    60

GCAGCAGGGC GAGAGGTTTC ATCGGGATTC CTTGGCAGTC TGAATGACGT GCCAGCCTAT   120

CAGCGCGGCG CCGGTGCGGC GAGGGCGCGC CGGACCCAGT GCGTCACCTC TCGTCTGATC   180

CGCCTCCCTC GACGGGCGTC GCTGACAAAA AAATTCAAAC AGAAATTAAC ATTTATGTCA   240

TTTACACCAA ACCGCATTTG TTGCAGAAT GCTCAAACGT GTGTTTGAAC AGAGCAAGCA    300

ACACGTAAAC AGGGATGACA TGCAGTACCC GTAAGAAGGG CCGATTGGCC CACAACAACA   360

CTGTTCTGCC GAACTGGAGA CCGATGATGA ATATGGACGT GATCAAGAGC TTTACCGAGC   420

AGATGCAAGG CTTCGCCGCC CCCCTCACCC GCTACAACCA GCTGCTGGCC AGCAACATCG   480

AACAGCTGAC CCGGTTGCAG CTGGCCTCCG CCAACGCCTA CGCCGAACTG GGCCTCAACC   540

AGTTGCAGGC CGTGAGCAAG GTGCAGGACA CCCAGAGCCT GGCGGCCCTG GCACAGTGC    600

AACTGGAGAC CGCCAGCCAG CTCTCCCGCC AGATGCTGGA TGACATCCAG AAGCTGAGCG   660

CCCTCGGCCA GCAGTTCAAG GAAGAGCTGG ATGTCCTGAC CGCAGACGGC ATCAAGAAAA   720

GCACGGGCAA GGCCTGATAA CCCCTGGCTG CCCGTTCGGG CAGCCACATC TCCCCATGAC   780

TCGACGCTAC GGGCTAGTTC CCGCCTCGGG TGTGGGTGAA GGAGAGCACA TGAGCCAACC   840

ATCTTATGGC CCGCTGTTCG AGGCCCTGGC CCACTACAAT GACAAGCTGC TGGCCATGGC   900

CAAGGCCCAG ACAGAGCGCA CCGCCCAGGC GCTGCTGCAG ACCAATCTGG ACGATCTGGG   960

CCAGGTGCTG GAGCAGGGCA GCCAGCAACC CTGGCAGCTG ATCCAGGCCC AGATGAACTG  1020

GTGGCAGGAT CAGCTCAAGC TGATGCAGCA CACCCTGCTC AAAAGCGCAG GCCAGCCGAG  1080

CGAGCCGGTG ATCACCCCGG AGCGCAGCGA TCGCCGCTTC AAGGCCGAGG CCTGGAGCGA  1140

ACAACCCATC TATGACTACC TCAAGCAGTC CTACCTGCTC ACCGCCAGGC ACCTGCTGGC  1200

CTCGGTGGAT GCCCTGGAGG GCGTCCCCCA GAAGAGCCGG GAGCGGCTGC GTTTCTTCAC  1260

CCGCCAGTAC GTCAACGCCA TGGCCCCCAG CAACTTCCTG GCCACCAACC CCGAGCTGCT  1320

CAAGCTGACC CTGGAGTCCG ACGGCCAGAA CCTGGTGCGC GGACTGGCCC TCTTGGCCGA  1380

GGATCTGGAG CGCAGCGCCG ATCAGCTCAA CATCCGCCTG ACCGACGAAT CCGCCTTCGA  1440

GCTCGGGCGG GATCTGGCCC TGACCCCGGG CCGGGTGGTG CAGCGCACCG AGCTCTATGA  1500

GCTCATTCAG TACAGCCCGA CTACCGAGAC GGTGGGCAAG ACACCTGTGC TGATAGTGCC  1560

GCCCTTCATC AACAAGTACT ACATCATGGA CATGCGGCCC CAGAACTCCC TGGTCGCCTG  1620

GCTGGTCGCC CAGGGCCAGA CGGTATTCAT GATCTCCTGG CGCAACCCGG GCGTGGCCCA  1680

GGCCCAAATC GATCTCGACG ACTACGTGGT GGATGGCGTC ATCGCCGCCC TGGACGGCGT  1740

GGAGGCGGCC ACCGGCGAGC GGGAGGTGCA CGGCATCGGC TACTGCATCG GCGGCACCGC  1800

CCTGTCGCTC GCCATGGGCT GGCTGGCGGC GCGGCGCCAG AAGCAGCGGG TGCGCACCGC  1860

CACCCTGTTC ACTACCCTGC TGGACTTCTC CCAGCCCGGG GAGCTTGGCA TCTTCATCCA  1920

CGAGCCCATC ATAGCGGCGC TCGAGGCGCA AAATGAGGCC AAGGGCATCA TGGACGGGCG  1980
```

-continued

```
CCAGCTGGCG GTCTCCTTCA GCCTGCTGCG GGAGAACAGC CTCTACTGGA ACTACTACAT      2040

CGACAGCTAC CTCAAGGGTC AGAGCCCGGT GGCCTTCGAT CTGCTGCACT GGAACAGCGA      2100

CAGCACCAAT GTGGCGGGCA AGACCCACAA CAGCCTGCTG CGCCGTCTCT ACCTGGAGAA      2160

CCAGCTGGTG AAGGGGAGC TCAAGATCCG CAACACCCGC ATCGATCTCG GCAAGGTGAA       2220

GACCCCTGTG CTGCTGGTGT CGGCGGTGGA CGATCACATC GCCCTCTGGC AGGGCACCTG      2280

GCAGGGCATG AAGCTGTTTG GCGGGAGCA GCGCTTCCTC CTGGCGGAGT CCGGCCACAT       2340

CGCCGGCATC ATCAACCCGC CGGCCGCCAA CAAGTACGGC TTCTGGCACA ACGGGGCCGA      2400

GGCCGAGAGC CCGGAGAGCT GGCTGGCAGG GGCGACGCAC CAGGGCGGCT CCTGGTGGCC      2460

CGAGATGATG GGCTTTATCC AGAACCGTGA CGAAGGGTCA GAGCCCGTCC CCGCGCGGGT      2520

CCCGGAGGAA GGGCTGGCCC CCGCCCCCGG CCACTATGTC AAGGTGCGGC TCAACCCCGT      2580

GTTTGCCTGC CAACAGAGG AGGACGCCGC ATG AGC GCA CAA TCC CTG GAA GTA       2634
                                 Met Ser Ala Gln Ser Leu Glu Val
                                  1               5

GGC CAG AAG GCC CGT CTC AGC AAG CGG TTC GGG GCG GCG GAG GTA GCC       2682
Gly Gln Lys Ala Arg Leu Ser Lys Arg Phe Gly Ala Ala Glu Val Ala
     10              15              20

GCC TTC GCC GCG CTC TCG GAG GAC TTC AAC CCC CTG CAC CTG GAC CCG       2730
Ala Phe Ala Ala Leu Ser Glu Asp Phe Asn Pro Leu His Leu Asp Pro
25              30              35                      40

GCC TTC GCC GCC ACC ACG GCG TTC GAG CGG CCC ATA GTC CAC GGC ATG       2778
Ala Phe Ala Ala Thr Thr Ala Phe Glu Arg Pro Ile Val His Gly Met
             45              50              55

CTG CTC GCC AGC CTC TTC TCC GGG CTG CTG GGC CAG CAG TTG CCG GGC       2826
Leu Leu Ala Ser Leu Phe Ser Gly Leu Leu Gly Gln Gln Leu Pro Gly
             60              65              70

AAG GGG AGC ATC TAT CTG GGT CAA AGC CTC AGC TTC AAG CTG CCG GTC       2874
Lys Gly Ser Ile Tyr Leu Gly Gln Ser Leu Ser Phe Lys Leu Pro Val
     75              80              85

TTT GTC GGG GAC GAG GTG ACG GCC GAG GTG GAG GTG ACC GCC CTT CGC       2922
Phe Val Gly Asp Glu Val Thr Ala Glu Val Glu Val Thr Ala Leu Arg
     90              95              100

GAG GAC AAG CCC ATC GCC ACC CTG ACC ACC CGC ATC TTC ACC CAA GGC       2970
Glu Asp Lys Pro Ile Ala Thr Leu Thr Thr Arg Ile Phe Thr Gln Gly
105             110             115                     120

GGC GCC CTC GCC GTG ACG GGG GAA GCC GTG GTC AAG CTG CCT               3012
Gly Ala Leu Ala Val Thr Gly Glu Ala Val Val Lys Leu Pro
             125             130

TAAGCACCGG CGGCACGCAG GCACAATCAG CCCGGCCCCT GCCGGGCTGA TTGTTCTCCC      3072

CCGCTCCGCT TGCCCCCTTT TTCGGGGCAA TTTGGCCCAG GCCCTTTCCC TGCCCCGCCT      3132

AACTGCCTAA AATGGCCGCC CTGCCGTGTA GGCATTCATC CAGCTAGAGG AATTC          3187
```

(2) INFORMATION FOR SEQ ID NO: 11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 11:

```
AGTTCCCGCC TCGGGTGTGG GTGAA                                              25
```

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 12:

GGCATATGCG CTCATGCGGC GTCCT          25

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 13:

GCCATATGAG CGCACAATCC CTGGAAGTAG          30

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 14:

CTGGGATCCG CCGGTGCTTA AGGCAGCTTG          30

(2) INFORMATION FOR SEQ ID NO: 15:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 15:

Ser Ala Gln Ser Leu Glu Val Gly Gln Lys Ala Arg Leu Ser Lys Arg
1            5                10              15

Phe Gly Ala Ala
        20

(2) INFORMATION FOR SEQ ID NO: 16:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 16:

```
Met Ser Ala Gln Ser Leu Glu Val Gly Gln Lys Ala Arg Leu Ser Lys
 1               5                  10                  15

Arg Phe Gly Ala Ala
             20
```

POLYESTER SYNTHASE GENE AND PROCESS FOR PRODUCING POLYESTER

FIELD OF THE INVENTION

The present invention relates to a polyester synthase gene, a recombinant vector containing the gene, a transformant carrying the recombinant vector, and a process for producing polyester by use of the transformant.

BACKGROUND OF THE INVENTION

It is known that a large number of microorganisms biosynthesize poly-3-hydroxybutyrate (P(3HB)) and store it in the form of ultrafine particles as an energy source in the body. P(3HB) extracted from microorganisms is a thermoplastic polymer with a melting temperature of about 180° C., and because of its excellent biodegradability and biocompatibility it is drawing attention as "green" plastic for preservation of the environment. Further, P(3HB) is "green" plastic which can be synthesized from regenerable carbon resources including sugars and vegetable oils by various microorganisms. However, P(3HB) is a highly crystalline polymer and thus has the problem in physical properties of inferior resistance to impact, so its practical application has never been attempted.

Recently, polyester P(3HB-co-3HH) as a random copolymer of 3-hydroxybutyrate (3HB) and 3-hydroxyhexanoate (3HH) and a process for producing the same have been studied and developed, and these are described in e.g. Japanese Patent Laid open Publication Nos. 93049/1993 and 265065/1995 respectively. In these publications, the P(3HB-co-3HH) copolymer is produced from alkanoic acids or olive oil by fermentation with *Aeromonas caviae* isolated from soil. It is revealed that because the degree of crystallinity of the P(3HB-co-3HH) copolymer produced through fermentation is reduced with an increasing ratio of the 3HH unit in it, so that the copolymer becomes a soft polymeric material excellent in thermostability and formability and can be manufactured into strong yarn or transparent flexible film (Y. Doi, S. Kitamura, H. Abe, Macromolecules 28, 4822–4823 (1995)). However, the yield of polyester (content of polyester in dried microorganisms) according to the processes described in Japanese Patent Laid open Publication Nos. 93049/1993 and 265065/1995 is low, and thus there is demand for developments in a process for producing the copolymerized polyester P(3HB-co-3HH).

SUMMARY OF THE INVENTION

The object of the present invention is to provide a polyester synthase gene, recombinant vectors containing the gene, transformants transformed with the recombinant vectors, and processes for producing polyester by use of the transformants.

As a result of their eager research, the present inventors succeeded in producing the polyester in high yield by cloning a polyester synthase gene and deleting one or both of open reading frames located upstream and downstream of said gene to arrive at the completion of the present invention.

That is, the present invention is a polyester synthase gene coding for a polypeptide containing the amino acid sequence of SEQ ID NO:2 or a sequence where in said amino acid sequence, one or more amino acids are deleted, replaced or added, said polypeptide bringing about polyester synthase activity. Said gene includes those containing e.g. the nucleotide sequence of SEQ ID NO:1.

Further, the present invention is a gene expression cassette comprising said polyester synthase gene and either of open reading frames located upstream and downstream of said gene. In said gene expression cassette, the open reading frame located upstream of the polyester synthase gene includes those (e.g. SEQ ID NO:3) containing DNA coding for the amino acid sequence of SEQ ID NO:4, and the open reading frame located downstream of the polyester synthase gene includes those (e.g. SEQ ID NO:5) containing DNA coding for a polypeptide containing the amino acid sequence of SEQ ID NO:6 or a sequence where in said amino acid sequence, one or more amino acids are deleted, replaced or added, said polypeptide bringing about enoyl-CoA hydratase activity.

Even if one or more amino acids in the amino acid sequence of SEQ ID NO:2 have undergone mutations such as deletion, replacement, addition etc., DNA coding for a polypeptide containing said amino acid sequence is also contained in the gene of the present invention insofar as the polypeptide has polyester synthase activity. For example, DNA coding for the amino acid sequence of SEQ ID NO:2 where methionine at the first position is deleted is also contained in the gene of the present invention.

Further, the present invention is recombinant vectors comprising said polyester synthase gene or said gene expression cassette.

Further, the present invention is transformants transformed with said recombinant vectors.

Further, the present invention is processes for producing polyester, wherein said transformant is cultured in a medium, and polyester is recovered from the resulting culture. Examples of such polyester are copolymers (e.g. poly(3-hydroxybutyrate-co-3-hydroxyhexanoate) random copolymers) of 3-hydroxyalkanoic acid represented by formula I:

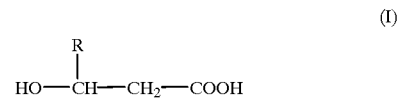

(I)

wherein R represents a hydrogen atom or a C1 to C4 alkyl group.

DETAILED DESCRIPTION OF THE INVENTION

Figure 1A:
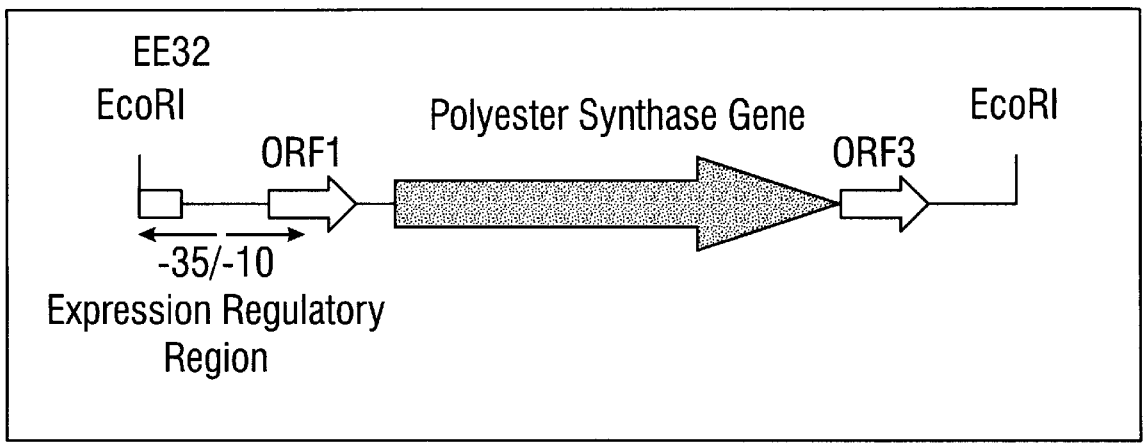
FIG. 1(A–D) shows the structure of the gene of the present invention.

Hereinafter, the present invention is described in detail.
(1) Cloning of Polyester Synthase Gene The polyester synthase gene of the present invention is separated from a microorganism belonging to the genus Aeromonas.

First, genomic DNA is isolated from a strain having the polyester synthase gene. Such a strain includes e.g. *Aeromonas caviae*.

Any known methods can be used for preparation of genomic DNA. For example, *Aeromonas caviae* is cultured in LB medium and then its genomic DNA is prepared by the hexadecyl trimethyl ammonium bromide method (Current Protocols in Molecular Biology, vol. 1, page 2.4.3., John Wiley & Sons Inc., 1994).

The DNA obtained in this manner is partially digested with a suitable restriction enzyme (e.g. Sau3AI, BamHI, BglII etc.) and then the DNA fragments are then dephosphorylated by treatment with alkaline phosphatase. It is ligated into a vector previously cleaved with a restriction enzyme (e.g. BamHI, BglII etc.) to prepare a library.

Phage or plasmid capable of autonomously replicating in host microorganisms is used as the vector. The phage vector includes e.g. EMBL3, M13, λgtll etc., and the plasmid vector includes e.g. pBR322, pUC18, and pBluescript II (Stratagene). Vectors capable of autonomously replicating in 2 or more host cells such as E. coli and Bacillus brevis, as well as various shuttle vectors, can also be used. Such vectors are also cleaved with said restriction enzymes so that their fragment can be obtained.

Conventional DNA ligase is used to ligate the resulting DNA fragments into the vector fragment. The DNA fragments and the vector fragment are annealed and then ligated to produce a recombinant vector.

To introduce the recombinant vector into a host microorganism, any known methods can be used. For example, if the host microorganism is E. coli, the calcium method (Lederberg, E. M. et al., J. Bacteriol. 119, 1072 (1974)) and the electroporation method (Current Protocols in Molecular Biology, vol. 1, page 1.8.4 (1994)) can be used. If phage DNA is used, the in vitro packaging method (Current Protocols in Molecular Biology, vol. 1,, page 5.7.1 (1994)) etc. can be adopted. In the present invention, an in vitro packaging kit (Gigapack II, produced by Stratagene etc.) can also be used.

To obtain a DNA fragment containing the polyester synthase gene derived from Aeromonas caviae, a probe is then prepared. The amino acid sequences of some polyester synthase have already been known (Peoples, O. P. and Sinskey, A. J., J. Biol. Chem., 264, 15293 (1989); Huisman, G. W. et al., J. Biol. Chem., 266, 2191 (1991); Pieper, U. et al., FEMS Microbiol. Lett., 96, 73 (1992) etc.). Two conserved regions are selected from these amino acid sequences, and nucleotide sequences coding them are estimated to design oligonucleotides for use as primers. Examples of such oligonucleotides include, but are not limited to, the 2 oligonucleotides 5'-CC(C/G)CC(C/G)TGGATCAA(T/C)AAGT (T/A)(T/C)TA(T/C)ATC-3' (SEQ ID NO:7) and 5'-(G/C)AGCCA (G/C)GC(G/C)GTCCA(A/G)TC(G/C)GGCCACCA-3' (SEQ ID NO:8).

Polymerase chain reaction (PCR) (Molecular Cloning, vol. 2, page 14.2 (1989)) is carried out using these oligonucleotides as primers and the genomic DNA of Aeromonas caviae as a template. The partial fragment of polyester synthase gene is amplified by PCR.

Then, the partially amplified fragment thus obtained is labeled with a suitable reagent and used for colony hybridization of the above genomic DNA library (Current Protocols in Molecular Biology, vol. 1, page 6.0.3 (1994)).

The E. coli is screened by colony hybridization, and a plasmid is recovered from it using the alkaline method (Current Protocols in Molecular Biology, vol. 1, page 1.6.1 (1994)), whereby a DNA fragment containing the polyester synthase gene is obtained.

The nucleotide sequence of said DNA fragment can be determined in e.g. an automatic nucleotide sequence analyzer such as 373A DNA sequencer (Applied Biosystems) using a known method such as the Sanger method (Molecular Cloning, vol. 2, page 13.3 (1989)).

The nucleotide sequence of the polyester synthase gene of the present invention is shown in SEQ ID NO:1, and the amino acid sequence encoded by said gene is shown in SEQ ID NO:2, where some amino acids may have undergone mutations such as deletion, replacement, addition etc. insofar as a polypeptide having said amino acid sequence brings about polyester synthase activity. Further, the gene of the present invention encompasses not only the nucleotide sequence coding for the amino acid sequence of SEQ ID NO:2 but also its degenerated which except for degeneracy codons, code for the same polypeptide.

The above mutations such as deletion etc. can be induced by known site-directed mutagenesis (Current Protocols in Molecular Biology, vol., 1, page 8.1.1 (1994)).

After the nucleotide sequence was determined by the means described above, the gene of the present invention can be obtained by chemical synthesis or the PCR technique using genomic DNA as a template, or by hybridization using a DNA fragment having said nucleotide sequence as a probe.

(2) Preparation of Transformant

The transformant of the present invention is obtained by introducing the recombinant vector of the present invention into a host compatible with the expression vector used in constructing said recombinant vector.

The host is not particularly limited insofar as it can express the target gene. Examples are bacteria such as microorganisms belonging to the genus Alcaligenes, microorganisms belonging to the genus Pseudomonas, microorganisms belonging to the genus Bacillus, yeasts such as the genera Saccharomyces, Candida etc., and animal cells such as COS cells, CHO cells etc.

If bacteria such as microorganisms belonging to the genus Alcaligenes, microorganisms belonging to the genus Pseudomonas etc. are used as the host, the recombinant DNA of the present invention is preferably constituted such that it contains a promoter, the DNA of the present invention, and a transcription termination sequence so as to be capable of autonomous replication in the host. The expression vector includes pLA2917 (ATCC 37355) containing replication origin RK2 and pJRD215 (ATCC 37533) containing replication origin RSF1010, which are replicated and maintained in a broad range of hosts.

The promoter may be any one if it can be expressed in the host. Examples are promoters derived from E. coli, phage etc., such as trp promoter, lac promoter, $P_L$ promoter, $P_R$ promoter and T7 promoter. The method of introducing the recombinant DNA into bacteria includes e.g. a method using calcium ions (Current Protocols in Molecular Biology, vol. 1, page 1.8.1 (1994)) and the electroporation method (Current Protocols in Molecular Biology, vol. 1, page 1.8.4 (1994)).

If yeast is used as the host, expression vectors such as YEp13, YCp50 etc. are used. The promoter includes e.g. gal 1 promoter, gal 10 promoter etc. To method of introducing the recombinant DNA into yeast includes e.g. the electroporation method (Methods. Enzymol., 194, 182–187 (1990)), the spheroplast method (Proc. Natl. Acad. Sci. USA, 84, 1929–1933 (1978)), the lithium acetate method (J. Bacteriol., 153, 163–168 (1983)) etc.

If animal cells are used as the host, expression vectors such as pcDNAI, pcDNAI/Amp (produced by Invitrogene) etc. are used. The method of introducing the recombinant DNA into animal cells includes e.g. the electroporation method, potassium phosphate method etc.

The nucleotide sequence determined as described above contains the polyester synthase gene as well as a plurality of open reading frames (ORFs) upstream and downstream of it. That is, the polyester synthase gene forms an operon with at least 2 ORFs under the control of a single promoter region.

The ORFs which are located respectively upstream and downstream of the polyester synthase gene are referred to hereinafter as "ORF1" and "ORF3".

It is considered that ORF1 is an open reading frame of a gene involved in accumulating polyester in the microorganism or a gene in the polyester biosynthesis system. It was revealed that ORF3 is an open reading frame of a gene coding for enoyl-CoA hydratase (particularly (R)-specific enoyl-CoA hydratase) involved in biosynthesis of polyester.

As shown in FIG. 1, an EcoRI fragment carrying an expression regulatory region (expressed as "−35/−10" in FIG. 1A), the polyester synthase gene, ORF1, and ORF3 was cloned in the present invention (FIG. 1A). This fragment is designated EE32.

Then, a fragment (a gene expression cassette) is prepared by deleting ORF1 and/or ORF3 from EE32, and this cassette is introduced into a host whereby a transformant capable of efficiently producing polyester can be obtained.

Figure 1B:
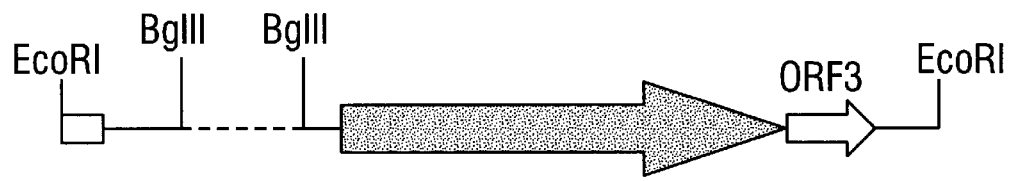
Figure 1C:
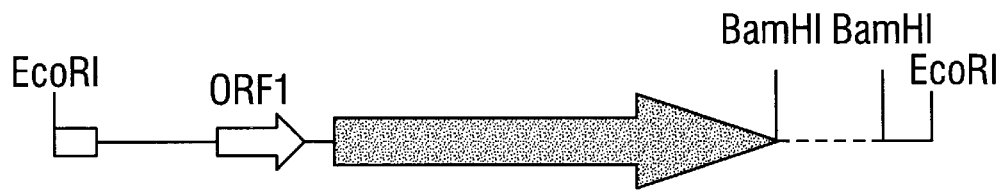

In EE32, a restriction enzyme BglII sites are introduced into regions between the expression regulatory region and the translation initiation codon of ORF1 and between the translation termination codon of ORF1 and the translation initiation codon of the polyester synthase gene, and then ORF1 is deleted from EE32 by treatment with BglII (FIG. 1B). Similarly, a restriction enzyme BamHI sites is introduced into a region between the translation termination codon of the polyester synthase gene and ORF3, and then ORF3 is deleted by treatment with BamHI (FIG. 1C).

Figure 1D:
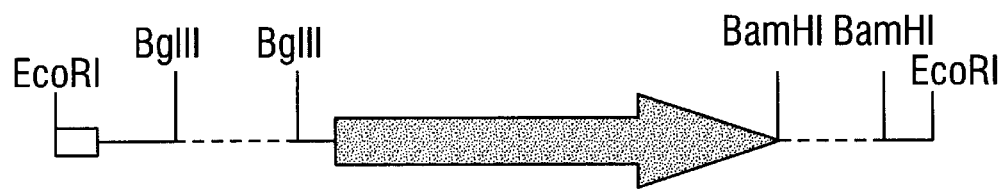

To delete both ORF1 and ORF3, EE32 may be subjected to the above operation of deleting ORF1 and ORF3 (FIG. 1D).

The restriction enzyme sites can be introduced by site-directed mutagenesis using synthetic oligonucleotides (Current Protocols in Molecular Biology, vol. 1, page 8.1.1 (1994)).

Each gene expression cassette thus obtained is inserted into said plasmid capable of expression (e.g. pJRD215 (ATCC 37533)) and the resulting recombinant vector is used to transform *Alcaligenes eutrophus* PHB-4 (DSM541) (strain deficient in the ability to synthesize polyester). The method for this transformation includes e.g. the calcium chloride method, rubidium chloride method, low pH method, in vitro packaging method, conjugation transfer method etc.

(3) Production of Polyester

The production of polyester is carried out by culturing the transformant of the present invention in a medium, forming and accumulating the polyester of the present invention in the microorganism or in the culture, and recovering the polyester from the cultured microorganism or from the culture.

A conventional method used for culturing the host is also used to culture the transformant of the present invention.

The medium for the transformant prepared from a microorganism belonging to the genus Alcaligenes or Pseudomonas as the host include a medium containing a carbon source assimilable by the microorganism, in which a nitrogen source, inorganic salts or another organic nutrition source has been limited, for example a medium in which the nutrition source has been limited to 0.01 to 0.1%.

The carbon source is necessary for growth of the microorganism, and it is simultaneously a starting material of polyester. Examples are hydrocarbons such as glucose, fructose, sucrose, maltose etc. Further, fat and oil related substances having 2 or more carbon atoms can be used as the carbon source. The fat and oil related substances include natural fats and oils, such as corn oil, soybean oil, safflower oil, sunflower oil, olive oil, coconut oil, palm oil, rape oil, fish oil, whale oil, porcine oil and cattle oil, aliphatic acids such as acetic acid, propionic acid, butanoic acid, pentanoic acid, hexoic acid, octanoic acid, decanoic acid, lauric acid, oleic acid, palmitic acid, linolenic acid, linolic acid and myristic acid as well as esters thereof, alcohols such as ethanol, propanol, butanol, pentanol, hexanol, octanol, lauryl alcohol, oleyl alcohol and palmityl alcohol as well as esters thereof.

The nitrogen source includes e.g. ammonia, ammonium salts such as ammonium chloride, ammonium sulfate, ammonium phosphate etc., peptone, meat extract, yeast extract, corn steep liquor etc. The inorganic matter includes e.g. monopotassium phosphate, dipotassium phosphate, magnesium phosphate, magnesium sulfate, sodium chloride etc.

Culture is carried out usually under aerobic conditions with shaking at 25 to 37° C. for more than 24 hours (e.g. 1 to 7 days) after expression is induced. During culture, antibiotics such as ampicillin, kanamycin, antipyrine, tetracycline etc. may be added to the culture. Polyester is accumulated in the microorganism by culturing it, and the polyester is then recovered.

To culture the microorganism transformed with the expression vector using an inducible promoter, its inducer can also be added to the medium. For example, isopropyl-β-D-thiogalactopyranoside (IPTG), indoleacrylic acid (IAA) etc. can be added to the medium.

To culture the transformant from animal cells as the host, use is made of a medium such as RPMI-1640 or DMEM which may be supplemented with fetal bovine serum. Culture is carried out usually in the presence of 5% $CO_2$ at 30 to 37° C. for 14 to 28 days. During culture, antibiotics such as kanamycin, penicillin etc. may be added to the medium.

In the present invention, purification of polyester can be carried out e.g. as follows:

The transformant is recovered from the culture by centrifugation, then washed with distilled water and dried. Thereafter, the dried transformant is suspended in chloroform and heated to extract polyester from it. The residues are removed by filtration. Methanol is added to this chloroform solution to precipitate polyester. After the supernatant is removed by filtration or centrifugation, the precipitates are dried to give purified polyester.

The resulting polyester is confirmed to be the desired one in a usual manner e.g. by gas chromatography, nuclear magnetic resonance etc.

The gene of the present invention contains the polyester synthase gene isolated from *Aeromonas caviae*. This synthase can synthesize a copolymer (polyester) consisting of a monomer unit 3-hydroxyalkanoic acid represented by formula I:

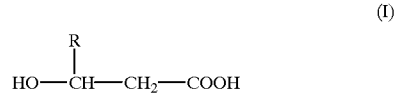

(I)

wherein R represents a hydrogen atom or a C1 to C4 alkyl group. Said copolymer includes e.g. poly(3-hydroxybutyrate-co-3-hydroxyhexanoate) random copolymer (P(3HB-co-3HH)) etc. and the transformant carrying said polyester synthase gene has the ability to produce P(3HB-co-3HH) with very high efficiency.

Conventionally, a process for producing poly-3-hydroxybutyrate (P(3HB)) or poly(3-hydroxybutyrate-co-3-hydroxyvalerate) random copolymer P(3HB-co-3HV) has been studied and developed, but such polyester has the problem in physical properties of inferior resistance to impact because it is a highly crystalline polymer.

Because degree of crystallinity is lowered by introducing 3-hydroxyhexanoate having 6 carbon atoms into a polymer chain, polyester acts as a flexible polymeric material which is also excellent in thermostability and formability, but conventional processes for producing P(3HB-co-3HH) by use of *Aeromonas caviae* (Japanese Patent Laid Open Publication Nos. 93049/1993 and 265065/1995) suffer from a low yield of polyester.

In the present invention, the P(3HB-co-3HH) copolyester can be produced in high yield.

Because the desired polyester can be obtained in a large amount using the above means, it can be used as a biodegradable material of yarn or film, various vessels etc. Further, the gene of the present invention can be used to breed a strain highly producing the P(3HB-co-3HH) copolymer polyester.

EXAMPLES

Hereinafter, the present invention is described in more detail with reference to the Examples which however are not intended to limit the scope of the present invention.

[Example 1] Cloning of the Polyester Synthase Gene from *Aeromonas caviae*

First, a genomic DNA library was prepared from *Aeromonas caviae*.

*Aeromonas caviae* FA440 was cultured overnight in 100 ml LB medium (1% yeast extract, 0.5% trypton, 0.5% sodium chloride, 0.1% glucose, pH 7.5) at 30° C. and then genomic DNA was obtained from the microorganism using the hexadecyl trimethyl ammonium bromide method (Current Protocols in Molecular Biology, vol. 1, page 2.4.3 (1994), John Wiley & Sons Inc.).

The resulting genomic DNA was partially digested with restriction enzyme Sau3AI. The vector plasmid used was cosmid vector pLA2917 (ATCC 37355).

This plasmid was cleaved with restriction enzyme BglII and dephosphorylated (Molecular Cloning, vol. 1, page 5.7.2 (1989), Cold Spring Harbor Laboratory) and then ligated into the partially digested genomic DNA fragment by use of DNA ligase.

*E. coli* S17-1 was transformed with this ligated DNA fragment by the in vitro packaging method (Current Protocols in Molecular Biology, vol. 1, page 5.7.2 (1994)) whereby a genomic DNA library from *Aeromonas caviae* was obtained.

To obtain a DNA fragment containing the polyester synthase gene from *Aeromonas caviae*, a probe was then prepared. Two well conserved regions were selected from known amino acid sequences of several polyester synthases, and nucleotide sequences coding for them were estimated, and 2 oligonucleotides 5'-CC(C/G)CC(C/G)TGGATCAA(T/C)AAGT (T/A)(T/C) TA(T/C)ATC-3' (SEQ ID NO:7) and 5'-(G/C)AGCCA(G/C)GC(G/C)GTCCA(A/G)TC(G/C) GGCCACCA-3' (SEQ ID NO:8) were synthesized.

The polyester synthase gene was partially amplified by PCR using these oligonucleotides as primers and the genomic DNA from *Aeromonas caviae* as a template. PCR was carried out using 30 cycles, each consisting of reaction at 94° C. for 30 seconds, 50° C. for 30 seconds, and 72° C. for 60 seconds.

Then, this partially amplified fragment was labeled with digoxigenin using a DIG DNA labeling kit (Boehringer Mannheim) and used as a probe.

Using the probe thus obtained, *E. coli* carrying a plasmid containing the polyester synthase gene was isolated by colony hybridization from the genomic DNA library from *Aeromonas caviae*. By recovering the plasmid from the *E. coli*, a DNA fragment containing the polyester synthase gene was obtained.

The nucleotide sequence of a 3.2 kbp BglII-EcoRI fragment from this fragment was determined by the Sanger method.

As a result, the nucleotide sequence of the 3.2 kb fragment as shown in SEQ ID NOs:9 or 10 was determined.

By further examining homology to this nucleotide sequence, the polyester synthase gene containing the nucleotide sequence (1785 bp) of SEQ ID NO:1 could be identified in this 3.2 kbp nucleotide sequence.

It should be understood that insofar as the protein encoded by the polyester synthase gene of the present invention has the function of gene expression for polyester polymerization, the nucleotide sequence of said gene may have undergone mutations such as deletion, replacement, addition etc.

In a fragment having the nucleotide sequence of SEQ ID NO:9 or 10, a 405 bp gene (ORF3) and a transcription termination region located downstream of the above 1785 bp nucleotide sequence, as well as a 354 bp gene (ORF1) and an expression regulatory region located upstream thereof were identified. The nucleotide sequence of ORF1 is shown in SEQ ID NO:4; the nucleotide sequence of ORF3 in SEQ ID NO:5; and the amino acid sequence encoded by ORF3 in SEQ ID NO:6.

ORF3 is an open reading frame of a gene coding for enoyl-CoA hydratase involved in biosynthesis of polyester. Insofar as a polypeptide having the amino acid sequence encoded by ORF3 has enoyl-CoA hydratase activity, particularly (R)-specific enoyl-CoA hydratase activity, said amino acid sequence may have undergone mutations such as deletion, replacement and addition of one or more amino acids.

In the nucleotide sequences of SEQ ID NOS:9 and 10, the expression regulatory region is located at the 1- to 383-positions and the transcription termination region at the 3010 to 3187- positions.

[Example 2] Preparation of *Alcaligenes eutrophus* Transformant

The BglII site of the BglII-EcoRI fragment containing this expression regulatory region, ORF1, the polyester synthase gene, ORF3, and the transcriptional termination region was made EcoRI-ended by use of an EcoRI linker whereby a 3.2 kb EcoRI-EcoRI fragment (EE32 fragment) was obtained. This fragment was inserted into plasmid pJRD215 (ATCC 37533) capable of expression in microorganisms belonging to the genus Alcaligenes, and the resulting recombinant plasmid was transformed into *Alcaligenes eutrophus* PHB-4 (DSM 541) (strain deficient in the ability to synthesize polyester) by the conjugation transfer method, as follows:

First, the recombinant plasmid was used to transform *E. coli* S17-1 by the calcium chloride method. The recombinant *E. coli* thus obtained and *Alcaligenes eutrophus* PHB-4 were cultured overnight in 1.5 ml LB medium at 30° C., and the respective cultures, each 0.1 ml, were combined and cultured at 30° C. for 4 hours. This microbial mixture was plated on MBF agar medium (0.9% disodium phosphate, 0.15% monopotassium phosphate, 0.05% ammonium chloride, 0.5% fructose, 1.5% agar, 0.3 mg/ml kanamycin) and cultured at 30° C. for 5 days.

Because *Alcaligenes eutrophus* PHB-4 is rendered resistant to kanamycin by transferring the plasmid in the recombinant *E. coli* into it, the colonies grown on the MBF agar medium are a transformant of *Alcaligenes eutrophus*. One colony was isolated from these colonies so that *Alcaligenes eutrophus* AC32 (referred to hereinafter as AC32) was obtained.

AC32 has been deposited as FERM BP-6038 with the National Institute of Bioscience and Human-Technology, Agency of Industrial Science and Technology, Japan. This culture was deposited on Aug. 12, 1996 under the terms of the Budapest Treaty.

A restriction enzyme BglII sites were introduced respectively into regions upstream and downstream of the ORF1 gene in the EE32 fragment by site-directed mutagenesis using a synthetic oligonucleotide (Current Protocols in Molecular Biology, vol. 1, page 8.1.1 (1994)), and an ORF1 gene-free fragment was obtained by deleting the BglII-BglII fragment from the EE32 fragment and then inserted into plasmid pJRD215. The resulting recombinant plasmid was used to transform *Alcaligenes eutrophus* PHB-4 by the conjugation transfer method described above. The resulting transformant is referred to hereinafter as AC321.

Similarly, a restriction enzyme BamHI sites were introduced respectively regions upstream and downstream of the ORF3 gene in the EE32 fragment by site-directed mutagenesis, and an ORF3 gene-free fragment was obtained by deleting the BamHI-BamHI fragment from the EE32 fragment and then inserted into plasmid pJRD215. The resulting recombinant plasmid was used to transform *Alcaligenes eutrophus* PHB-4 by the conjugation transfer method described above. The resulting transformant is referred to hereinafter as AC323.

Similarly, a restriction enzyme BglII sites were introduced respectively regions upstream and downstream of the ORF1 gene and a restriction enzyme BamHI sites were introduced respectively regions upstream and downstream of the ORF3 gene in the EE32 fragment, and a gene fragment free of both the ORF1 and ORF3 genes was obtained by deleting the BglII-BglII and BamHI-BamHI fragments from the EE32 fragment and then inserted into plasmid pJRD215. The resulting recombinant plasmid was used to transform *Alcaligenes eutrophus* PHB-4 by the conjugation transfer method described above. The resulting transformant is referred to hereinafter as AC3213.

Further, the polyester synthase gene was amplified by PCR using the EE32 fragment as a template, and the resulting amplification product was inserted into a region between an expression regulatory region and a transcription termination region in a known polyester biosynthesis operon derived from *Alcaligenes eutrophus*. PCR was carried out using 5'-AGTTCCCGCCTCGGGTGTGGGTGAA-3' (SEQ ID NO:11) and 5'-GGCATATGCGCTCATGCGGCGTCCT-3' (SEQ ID NO:12) as primers in 30 cycles each consisting of reaction at 94° C. for 30 seconds, 55° C. for 30 seconds and 72° C. for 60 seconds.

This DNA fragment was inserted into plasmid pJRD215, and the resulting plasmid was used to transform *Alcaligenes eutrophus* PHB-4 by the conjugation transfer method described above. The resulting transformant is referred to hereinafter as AC29.

[Example 3] Synthesis of Polyester by *Alcaligenes eutrophus* Transformants

Each of *Alcaligenes eutrophus* H16, PHB-4, AC32, AC321, AC323, AC3213 and AC29 was inoculated into 95 ml MB medium (0.9% disodium phosphate, 0.15% monopotassium phosphate, 0.05% ammonium chloride) containing 1 ml of 1% sodium octanate and incubated in a flask at 30° C. 0.2 g/L kanamycin was contained in the mediums for strains AC32, AC321, AC323, AC3213 and AC29. 12, 24, 36 and 48 hours thereafter, 1 ml of 1% sodium octanate was added to each medium (total amount of sodium octanate added: 0.5 g) and the microorganisms were cultured for 72 hours.

Each of strains H16 and AC3213 was inoculated into the above MB medium to which 1% olive oil, palm oil, corn oil or oleic acid had been added, and each strain was cultured at 30° C. for 72 hours in a flask. 0.2 g/L kanamycin was contained in the mediums for strain AC3213.

Each of strains H16, AC32, AC321, AC323 and AC3213 was inoculated into the above MB medium to which 1% sodium heptanoate had been added, and each strain was cultured at 30° C. in a flask. 0.2 g/L kanamycin was contained in the mediums for strains AC32, AC321, AC323 and AC3213.

While 1 ml of 1% sodium heptanoate was added to each medium (total amount of sodium heptanoate added: 0.5 g) 12, 24, 36 and 48 hours thereafter, the microorganisms were cultured for 72 hours. 444

The microorganisms were recovered by centrifugation, washed with distilled water and lyophilized, and the weight of the dried microorganisms was determined. 2 ml sulfuric acid/methanol mixture (15:85) and 2 ml chloroform were added to 10–30 mg of the dried microorganism, and the sample was sealed and heated at 100° C. for 140 minutes whereby the polyester in the microorganisms was decomposed into methylester. 1 ml distilled water was added thereto and stirred vigorously. It was left and separated into 2 layers, and the lower organic layer was removed and analyzed for its components by capillary gas chromatography through a capillary column Neutra BOND-1 (column of 25 m in length, 0.25 mm in inner diameter and 0.4 μm in liquid film thickness, manufactured by GL Science) in Shimadzu GC-14A. The temperature was raised at a rate of 8° C./min. from an initial temperature of 100° C. The results are shown in Tables 1, 2 and 3.

TABLE 1

Synthesis of Polyester Using Octanoic Acid as Carbon Source

| Strain Used A. eutrophus | Weight of Dried Microorganism (g/l) | Content of Polyester in Dried Microorganism (weight-%) | Polyester Comp. 3HB (mole-%) | 3HH (mole-%) |
|---|---|---|---|---|
| H16 | 3.00 | 86 | 100 | 0 |
| PHB-4 | 0.80 | 0 | — | — |
| AC32 | 0.99 | 33 | 78 | 23 |
| AC321 | 2.85 | 92 | 87 | 13 |
| AC323 | 2.85 | 92 | 88 | 12 |
| AC3213 | 3.64 | 96 | 85 | 15 |
| AC29 | 3.20 | 94 | 92 | 8 |

3HB: 3-hydroxybutyrate, 3HH: 3-hydroxyhexanoate

TABLE 2

Synthesis of Polyester Using Vegetable Oil or Oleic Acid as Carbon Source

| Strain Used A. eutrophus | Carbon Source | Weight of Dried Microorganism (g/l) | Content of Polyester in Dried Microorganism (weight-%) | Polyester Comp. 3HB (mole-%) | 3HH (mole-%) |
|---|---|---|---|---|---|
| H16 | olive oil | 4.27 | 79 | 100 | 0 |
|  | corn oil | 3.57 | 81 | 100 | 0 |
|  | palm oil | 4.13 | 79 | 100 | 0 |
|  | oleic acid | 4.06 | 82 | 100 | 0 |
| AC3213 | olive oil | 3.54 | 76 | 96 | 4 |
|  | corn oil | 3.60 | 77 | 95 | 5 |
|  | palm oil | 3.58 | 81 | 96 | 4 |
|  | oleic acid | 2.22 | 70 | 96 | 4 |

3HB: 3-hydroxybutyrate, 3HH: 3-hydroxyhexanoate

TABLE 3

Synthesis of Polyester Using Heptanoic Acid as Carbon Source

| Strain Used A. eutrophus | Weight of Dried Microorganism (g/l) | Content of Polyester in Dried Microorganism (weight-%) | Polyester Comp. | | |
|---|---|---|---|---|---|
| | | | 3HB | 3HV (mole-%) | 3HHp |
| H16 | 2.50 | 60 | 50 | 50 | 0 |
| AC32 | 0.77 | 7 | 30 | 67 | 5 |
| AC321 | 1.67 | 55 | 46 | 52 | 2 |
| AC323 | 1.27 | 40 | 48 | 45 | 7 |
| AC3213 | 2.76 | 67 | 44 | 48 | 8 |

3HB: 3-hydroxybutyrate, 3HH: 3-hydroxyhexanoate, 3HHp: 3-hydroxyheptanoate

As shown in Table 1, H16 (i.e. wild-type *Alcaligenes eutrophus*) synthesized a poly(3-hydroxybutyrate) homopolymer. This is because 3HH (3-hydroxyhexanoate) having 6 carbon atoms does not serve as a substrate for the polyester synthase possessed by H16. PHB-4 (i.e. the same strain as H16 but deficient in the ability to synthesize polyester) lacks the polyester synthase and thus does not accumulate polyester. AC32 prepared by introducing into PHB-4 the EE32 fragment containing the polyester synthase gene derived from *Aeromonas caviae* accumulated the poly (3-hydroxyburylate-co-3-hydroxyhexanoate) random copolymer (P(HB-co-3HH)) containing 22 mole-% 3HH (3-hydroxyhexanoate), and this copolymer accounted for 33% by weight of the dried microorganism.

AC321, AC323 and AC3213 accumulated P(3HB-co-3HH) containing 12 to 15 mole-% 3HH, and the copolymer accounted for 92 to 96% by weight of the dried microorganisms. As can be seen from these results, the ability of these strains to accumulate polyester was significantly improved by deleting the ORF1 gene and/or ORF3 gene.

P(3HB-co-3HH) was also accumulated in an amount of 94% by weight of the microorganism even in the case of AC29 carrying the polyester synthase gene derived from *A. caviae* whose expression regulatory region and transcriptional termination region had been replaced by those derived from *Alcaligenes eutrophus*, indicating that the yield of polyester was significantly improved even using the expression regulatory region and transcriptional termination region of different origin.

When AC3213 producing polyester in the highest yield was cultured using olive oil, corn oil or palm oil as a carbon source, the microorganism accumulated P(3HB-co-3HH) containing 4 to 5 mole-% 3HH, where the copolymer accounted for 76 to 81% by weight of the microorganism, as shown in Table 2. Even if oleic acid as an fatty acid component contained most abundantly in vegetable oils was used as a carbon source, AC3213 accumulated P(3HB-co-3HH) containing 4 mole-% 3HH, where the copolymer accounted for 70% by weight of the microorganism. Its corresponding wild strain H16 synthesized only poly(3-hydroxybutyrate) homopolymer under the same conditions.

*Alcaligenes eutrophus* FA440 is reported to have accumulated 8% by weight of P(3HB-co-3HH) by use of palmitic acid as a carbon source (Japanese Patent Laid Open Publication No. 265065/1995). On the other hand, the transformant according to the present invention has accumulated 96% by weight of P(3HB-co-3HH) by use of octanoic acid as a carbon source and 76 to 81% by weight of P(3HB-co-3HH) by use of extremely cheap vegetable oils as a carbon source, so the comparison therebetween indicates that the method of synthesizing P(3HB-co-3HH) by the transformant used in the present example is an extremely superior method.

When heptanoic acid was used as a carbon source, H16, that is a wild strain of *Alcaligenes eutrophus*, synthesized poly(3-hydroxybutyrate-co-3-hydroxyvalerate) copolymer (P(3HB-co-3HV)). This is because 3HHp (3-hydroxyheptanoate) having 7 carbon atoms does not serve as a substrate for the polyester synthase possessed by H16. AC32, derived from PHB-4 by introduction of the EE32 fragment containing the polyester synthase gene derived from *Aeromonas caviae*, accumulated poly(3-hydroxybutyrate-co-3-hydroxyvalerate-co-3-hydroxyheptanoate) terpolymer (P(3HB-co-3HV-co-3HHp)) containing 5 mole-% 3HHp, where this copolymer accounted for 7% by weight of the dried microorganism.

Further, each of strains AC321, AC323 and AC3213 accumulated P(3HB-co-3HV-co-3HHp) containing 2 to 8 mole-% 3HHp where the copolymer accounted for 40 to 67% by weight of the microorganisms, indicating that the yield of polyester was significantly improved by deleting the ORF1 gene and/or ORF3 gene (Table 3).

From these results, it is concluded that copolyesters consisting of 3-hydroxyalkanoic acid with 4 to 7 carbon atoms can be synthesized using the polyester synthase derived from *Aeromonas caviae*.

[Example 4] Identification of Functions of ORF3

The ORF3 gene was amplified by PCR using the EE32 fragment as a template and then inserted into a site downstream of T7 promoter in expression plasmid PET-3a (Novagene). PCR was carried out using 5'-GCCATATGAGCGCACAATCCCTGGAAGTAG-3' (SEQ ID NO:13) and 5'-CTGGGATCCGCCGGTGCTTAAGGCAGCTTG-3' (SEQ ID NO:14) as primers in 25 cycles each consisting of reaction at 95° C. for 60 seconds and 68° C. for 30 seconds. The resulting plasmid was used to transform *E. coli* BL21 (DE3) (Novagene). The resulting transformant is designated NB3.

NB3 was cultured in LB medium at 30° C. for 4 hours, and isopropyl-β-D-thiogalactopyranoside (IPTG) was added at a final concentration of 0.4 mM to induce expression, and it was further cultured at 30° C. for 2 hours. The microorganism was recovered by centrifugation, disrupted by ultrasonication and centrifuged to give a soluble protein fraction.

As shown in Table 4, high enoyl-CoA hydratase activity was detected in the soluble fraction from the microorganism having the expression plasmid introduced into it.

TABLE 4

| Specific Activity of Enoyl-CoA Hydratase in Soluble Protein Fraction | |
|---|---|
| | (unit/mg protein) |
| *E. coli* BL21/PET-3a | 0 |
| *E. coli* NB3 | 1700 |

The enoyl-CoA hydratase activity was determined by measuring a change in absorbance (263 nm) due to double bond hydration, using crotonyl-CoA (Sigma) as substrate (concentration: 0.25 mM). No activity was detected in *E. coli* into which the control plasmid PET-3a free of the ORF3 gene had been introduced.

Figure 2:
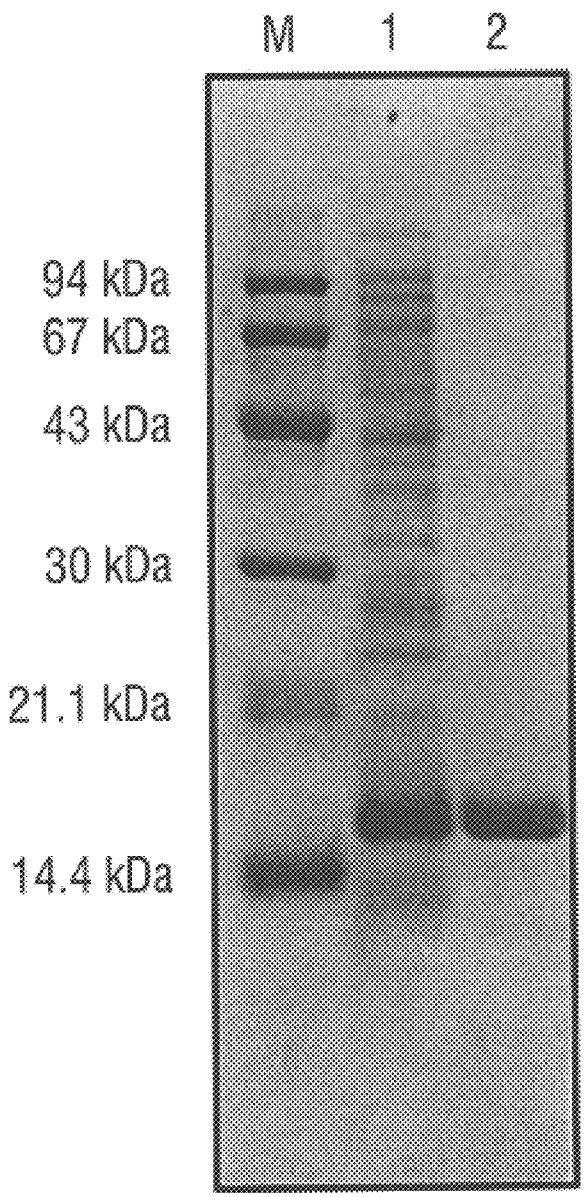
FIG. 2 is a photograph showing the result of SDS-polyacrylamide gel electrophoresis.

Then, the enoyl-COA hydratase protein was purified. A soluble protein fraction from NB3 was applied to an anion exchange column Q-Sepharose (Pharmacia) and eluted with a gradient of (0 to 1 M) NaCl, and a fraction with enoyl-CoA hydratase activity was collected. SDS-PAGE analysis indicated that the active fraction was homogenous in electrophoresis as shown in FIG. 2. In addition, about 3-fold specific activity could be attained as shown in Table 5.

TABLE 5

Specific Activity of Enoyl-CoA Hydratase

|  | (unit/mg protein) |
| --- | --- |
| E. coli NB3 soluble protein fraction | 1700 |
| anion exchange column elution fraction | 5100 |

The N-terminal amino acid sequence of the enoyl-CoA hydratase protein thus purified was determined. As shown in Table 6, the determined amino acid sequence was the same except for Met in the initiation codon as the amino acid sequence deduced from the nucleotide sequence of the ORF3 gene.

TABLE 6

Comparison between Amino Acid Sequences (unit/mg protein)

N-terminal amino acid sequence of
purified enoyl-CoA hydratase:
SAQSLEVGQKARLSKRFGAA (SEQ ID NO: 15)
amino acid sequence deduced from
ORF3 nucleotide sequence:
MSAQSLEVGQKARLSKRFGAA (SEQ ID NO: 16)

From this, it could be confirmed that ORF3 codes for enoyl-CoA hydratase. It is considered that Met was released by post-translational modification.

Further, the stereospecificity of enoyl-CoA hydratase encoded by ORF3 was examined as follows:

By adding (S)-3-hydroxybutyryl-CoA dehydrogenase (Sigma) (final concentration: 0.2 unit/ml) and oxidized nicotinamide adenine dinucleotide (NAD+) (final concentration: 0.5 mM) to a reaction solution for activity measurement, (S)-3-hydroxybutyryl-CoA formed is oxidized to acetoacetyl-CoA by the action of the dehydrogenase if the enoyl-CoA hydratase is specific to the (S)-isomer. During this reaction, NAD+ is reduced to form NADH resulting in the generation of a specific absorption at 340 nm. If enoyl-CoA hydratase is specific to the (R)-isomer, NADH is not formed.

As shown in Table 7, the change in absorbance at 340 nm when enoyl-CoA hydratase encoded by ORF3 was used, was the same as in the case where enoyl-CoA hydratase was absent, but if commercially available (S)-specific enoyl-CoA hydratase (Sigma) was used, a change in absorbance due to formation of NADH was observed.

TABLE 7

Change in Absorbance at 340 nm after 1 Min.

| no addition of enoyl-CoA hydratase | 0.045 |
| --- | --- |
| ORF3-derived enoyl-CoA hydratase | 0.047 |
| (S)-isomer specific enoyl-CoA hydratase (Sigma) | 0.146 |

From this result, it was made evident that the purified enoyl-CoA hydratase is specific to the (R)-isomer. Thus, it was found that ORF3 codes for (R)-isomer specific enoyl-CoA hydratase.

According to the present invention, there are provided a polyester synthase, a recombinant vector carrying the gene, a transformant carrying the recombinant vector and a process for producing polyester by use of the transformant.

The present invention is extremely useful in that the present gene codes for a polyester synthase capable of synthesizing polyester as a copolymer consisting of a monomer unit represented by 3-hydroxyalkanoic acid having 4 to 7 carbon atoms, and that the present process can synthesize a biodegradable plastic P(3HB-co-3HH) very efficiently which is excellent in thermostability and formability.

What is claimed is:

1. An isolated polyester synthase gene coding for a polypeptide containing the amino acid sequence of SEQ ID NO:2 or an enzymatically active fragment thereof.

2. An isolated polyester synthase gene comprising the nucleotide sequence of SEQ ID NO:1.

3. A gene expression cassette comprising the polyester synthase gene of claims 1 or 2 and either of open reading frames located upstream and downstream of said gene.

4. The gene expression cassette according to claim 3, wherein the open reading frame located upstream of the polyester synthase gene comprises DNA coding for the amino acid sequence of SEQ ID NO:4.

5. The gene expression cassette according to claim 3, wherein the open reading frame located upstream of the polyester synthase gene comprises the nucleotide sequence of SEQ ID NO:3.

6. The gene expression cassette according to claim 3, wherein the open reading frame located downstream of the polyester synthase gene comprises DNA coding for a polypeptide containing the amino acid sequence of SEQ ID NO:6 or a sequence where in said amino acid sequence, one or more amino acids are deleted, replaced or added, said polypeptide bringing about enoyl-CoA hydratase activity.

7. The gene expression cassette according to claim 3, wherein the open reading frame located downstream of the polyester synthase gene comprises the nucleotide sequence of SEQ ID NO:5.

8. A recombinant vector comprising the polyester synthase gene of claim 1.

9. A transformant transformed with the recombinant vector of claim 8.

10. A process for producing polyester, wherein the transformant of claim 9 is cultured in a medium and polyester is recovered from the resulting culture.

11. The process for producing polyester according to claim 10, wherein the polyester is a copolymer of 3-hydroxyalkanoic acid represented by formula I:

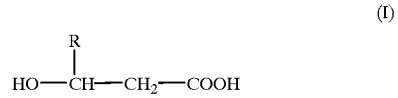

(I)

wherein R represents a hydrogen atom or a C1 to C4 alkyl group.

12. The process for producing polyester according to claim 10, wherein the polyester is a poly(3-hydroxybutyrate-co-3-hydroxyhexanoate) random copolymer.

13. A recombinant vector comprising the gene expression cassette of claim 3.

* * * * *